(12) United States Patent
Schmeder

(10) Patent No.: US 10,912,457 B2
(45) Date of Patent: Feb. 9, 2021

(54) LIGHTING SYSTEM FOR SIMULATING CONDITIONS OF COLOR DEFICIENT VISION AND DEMONSTRATING EFFECTIVENESS OF COLOR-BLINDNESS COMPENSATING EYEWEAR

(71) Applicant: ENCHROMA, INC., Berkeley, CA (US)

(72) Inventor: Andrew Schmeder, Richmond, CA (US)

(73) Assignee: EnChroma, Inc., Berkley, CA (US)

(*) Notice: Subject to any disclaimer, the term of this patent is extended or adjusted under 35 U.S.C. 154(b) by 611 days.

(21) Appl. No.: 15/725,206

(22) Filed: Oct. 4, 2017

(65) Prior Publication Data
US 2018/0098694 A1    Apr. 12, 2018

Related U.S. Application Data

(60) Provisional application No. 62/405,467, filed on Oct. 7, 2016.

(51) Int. Cl.
*A61B 3/06* (2006.01)
*A61H 5/00* (2006.01)
*G02C 7/10* (2006.01)

(52) U.S. Cl.
CPC .............. *A61B 3/066* (2013.01); *A61H 5/00* (2013.01); *A61H 2201/0188* (2013.01);
(Continued)

(58) Field of Classification Search
CPC .. A61B 3/066; A61B 3/06; A61H 5/00; A61H 2201/0188; A61H 2201/1604; A61H 2201/1602; A61H 2201/16; A61H 2201/5007; A61H 2201/5002; A61H 2201/50; A61H 2201/5025; A61H 2201/5023; A61H 2201/5092; A61H 2201/5094; A61H 2201/5097; A61H 2205/024; G02C 7/104; G02C 7/10; F21K 9/64; F21Y 2113/17; F21Y 2115/10; H01L 25/0753; H01L 33/50; H01L 33/504; H01L 2224/48091; H01L 2224/73265; H01L 2924/181; H05B 33/0857
See application file for complete search history.

(56) References Cited

U.S. PATENT DOCUMENTS 3,877,797 A    4/1975    Thornton, Jr.
4,176,299 A    11/1979    Thornton, Jr.
(Continued)

FOREIGN PATENT DOCUMENTS

CN    1165967 A    11/1997
CN    101203777 A    6/2008
(Continued)

OTHER PUBLICATIONS

International Search Report corresponding to PCTUS2017/055200, dated Nov. 30, 2017, 1 page.
(Continued)

*Primary Examiner* — John R Lee (57) ABSTRACT

The invention generally relates to devices that demonstrate the function of ophthalmic lenses that modify human color perception and to methods and devices that simulate color vision deficiency or color blindness.

16 Claims, 7 Drawing Sheets

(52) U.S. Cl.
CPC .............. *A61H 2201/1604* (2013.01); *A61H 2201/5007* (2013.01); *A61H 2201/5025* (2013.01); *A61H 2201/5092* (2013.01); *A61H 2201/5094* (2013.01); *A61H 2201/5097* (2013.01); *A61H 2205/024* (2013.01); *G02C 7/104* (2013.01)

(56) References Cited

U.S. PATENT DOCUMENTS

| | | | |
|---|---|---|---|
| 4,300,819 A | 11/1981 | Taylor | |
| 4,826,286 A | 5/1989 | Thornton, Jr. | |
| 4,966,453 A * | 10/1990 | Chang | A61B 3/066 351/242 |
| 5,270,854 A | 12/1993 | Lee et al. | |
| 5,369,453 A | 11/1994 | Chen et al. | |
| 5,408,278 A | 4/1995 | Christman | |
| 5,528,431 A | 6/1996 | Wilkins | |
| 5,646,781 A | 7/1997 | Johnson, Jr. | |
| 5,684,563 A * | 11/1997 | White | G09B 19/00 355/32 |
| 5,774,202 A | 6/1998 | Abraham et al. | |
| 6,132,044 A | 10/2000 | Sternbergh | |
| 6,145,984 A | 11/2000 | Farwig | |
| 6,149,270 A | 11/2000 | Hayashi | |
| 6,450,652 B1 | 9/2002 | Karpen | |
| 7,106,509 B2 | 9/2006 | Sharp | |
| 7,284,856 B2 | 10/2007 | Duha et al. | |
| 7,380,940 B2 * | 6/2008 | Anderson | A61B 3/066 351/200 |
| 7,393,100 B2 | 7/2008 | Mertz | |
| 7,506,977 B1 | 3/2009 | Aiiso | |
| 7,597,441 B1 | 10/2009 | Farwig | |
| 8,210,678 B1 | 7/2012 | Farwig | |
| 2002/0126256 A1 | 9/2002 | Larson | |
| 2004/0114242 A1 | 6/2004 | Sharp | |
| 2005/0224703 A1 | 10/2005 | Harada et al. | |
| 2006/0146275 A1 | 7/2006 | Mertz | |
| 2008/0212319 A1 | 9/2008 | Klipstein | |
| 2010/0179790 A1 | 7/2010 | Nakauchi et al. | |
| 2010/0182678 A1 | 7/2010 | Southwell | |
| 2010/0309647 A1 | 12/2010 | Winkler et al. | |
| 2011/0068698 A1 | 3/2011 | Swoboda et al. | |
| 2011/0090453 A1 * | 4/2011 | Chen | G02C 7/104 351/159.65 |
| 2011/0255051 A1 | 10/2011 | McCabe et al. | |
| 2012/0002168 A1 * | 1/2012 | Bonnin | G01M 11/0257 351/222 |
| 2012/0206050 A1 | 8/2012 | Spero | |
| 2013/0141693 A1 | 6/2013 | McCabe et al. | |
| 2013/0252000 A1 | 9/2013 | Takiff et al. | |
| 2014/0233105 A1 | 8/2014 | Schmeder et al. | |
| 2015/0235386 A1 * | 8/2015 | Wertheim | G06T 11/001 345/593 |
| 2015/0292690 A1 * | 10/2015 | Shpizel | F21V 13/12 250/504 R |
| 2017/0079527 A1 * | 3/2017 | Daneshi Kohan | A61B 3/0025 |
| 2018/0098694 A1 * | 4/2018 | Schmeder | A61H 5/00 |
| 2018/0128431 A1 * | 5/2018 | Heilman | F21K 9/275 |

FOREIGN PATENT DOCUMENTS

| | | |
|---|---|---|
| CN | 101690248 A | 3/2010 |
| EP | 0519660 A1 | 12/1992 |
| EP | 0939329 A1 | 9/1999 |
| EP | 1986024 A1 | 10/2008 |
| EP | 1340115 B1 | 5/2009 |
| JP | 2005511457 A | 4/2005 |
| JP | 2008282757 A | 11/2008 |
| WO | 95/05621 A1 | 2/1995 |
| WO | 02/42829 A1 | 5/2002 |
| WO | 02/094595 | 11/2002 |
| WO | 2006/071734 A2 | 7/2006 |
| WO | 2007094338 A1 | 8/2007 |
| WO | 2010/047952 A1 | 4/2010 |
| WO | 2013/022744 A2 | 2/2013 |
| WO | 2015/179538 A1 | 11/2015 |
| WO | 2016/148984 A1 | 9/2016 |

OTHER PUBLICATIONS

ANSI Z80.3-2010; The Accredited Committee Z80 for Ophthalmic Standards; American Standard for Ophthalmics—Nonprescription Sunglass and Fashion Eyewear Requirements; Jun. 7, 2010; pp. 1-24 (34 pages.
British Standard BS EN 1836:2005, Technical Committee CEN/TC 85 "Eye-protective equipment" Personal eye equipment—Sunglasses and sunglare filters for general use and filters for direct observation of the sun; Sep. 2007; pp. 1-34 (46 pages).
Rea, M.S. et al., Color Rendering: Beyond Pride and Prejudice; Color Research and Application, Dec. 2010; pp. 401-409; vol. 35; No. 6, 2010 Wiley Periodical, Inc.
Drum, Bruce; FDA regulation of labeling and promotional claims in the therapeutic color vision devices; A tutorial; Visual Neuroscience (2004), 21; pp. 461-463.
Tilsch, Markus K., et al., Manufacturing of precision optical coatings; Chinese Optics Letters, vol. 8, Supplement; Apr. 30, 2010; pp. 38-43.
Moreland, Jack D., et al., Quantitative assessment of commercial filter 'aids' for red-green colour defectives; Ophthal. Physiol. Opt. 2010 30: No. 5; pp. 685-692.
Vorobyev, Misha, et al., Receptor noise as a determinant of colour thresholds; Proc. R. Soc. Lond. B (1998) 265; pp. 351-358.
Sharp, G.D., et al., Retarder Stack Technology for Color Manipulation; 1999 SID International Symposium Digest of Technical Papers; May 1999; pp. 1072-1075.
PCT/US2012/027790; filed Mar. 5, 2012; Written Opinion of the International Searching Authority and International Search Report; 20 pages; dated Jul. 27, 2012.
PCT/US2012/027790; filed Mar. 5, 2012; International Preliminary Report on Patentability (1 pg.) dated Sep. 3, 2013 and Written Opinion (14 pgs.); dated Jul. 27, 2012.
Kirkpatrick, S., et al., Optimization by Simulated Annealing; Science, vol. 22, No. 4598, May 13, 1983, pp. 671-680.
Linear Programming; Feb. 28, 2011 (Feb. 28, 2011); XP055027872; Retrieved from the Internet: [on May 23, 2012] URL: http://en/wikipedia.org/w/index.php?title=Linear_programming&oldid=416428507.
Swillam, Mohammed A., et al., Multilayer Optical Coatings Using Convex Optimization; Journal of Lightwave Technology, IEEE Service Center, New York, NY, US; vol. 25, No. 4, Apr. 1, 2007; pp. 1078-1085.
European Extended Search Report corresponding to EP 14165905. 2; dated Jan. 2015; 15 pages.
International Search Report corresponding to PCT/US2016/051542, dated Dec. 5, 2016, 1 page.
USPTO Certificate of Correction, U.S. Pat. No. 5,528,431, issue date: Jun. 18, 1996 to Wilkins, to correct the name of the Assignee to: "Cerium Visual Technologies Limited, Kent, England and the Medical Research Council, Long, England", Aug. 19, 1997, 1 page.
Supplementary European Search Report corresponding to EP17859142, May 8, 2020, 6 pages.

* cited by examiner

| Index | Munsell Notation | Munsell Description | Reference CIE xy | Description with Y+B Light | Description with Y+B+W Light | Y+B+W with Glasses |
|---|---|---|---|---|---|---|
| Row 1: Natural Colors | | | | | | |
| 1 | 3 YR 3.7/3.2 | Dark skin | 0.400, 0.350 | Brown | Brown | Brown |
| 2 | 2.2 YR 6.47/4.1 | Light skin | 0.377, 0.345 | Beige | Beige | Light Tan |
| 3 | 4.3 PB 4.95/5.5 | Blue sky | 0.247, 0.251 | Light Blue | Light Blue | Light Blue |
| 4 | 6.7 GY 4.2/4.1 | Foliage | 0.337, 0.422 | Brown | Brown | Forest Green |
| 5 | 9.7 PB 5.47/6.7 | Blue flower | 0.265, 0.240 | Light Blue | Light Blue | Lavender |
| 6 | 2.5 BG 7/6 | Bluish green | 0.261, 0.343 | Light Blue-Gray | Light Blue-Gray | Light Cyan |
| Row 2: Miscellaneous Colors | | | | | | |
| 7 | 5 YR 6/11 | Orange | 0.506, 0.407 | Yellow | Yellow | Light Orange |
| 8 | 7.5 PB 4/10.7 | Purplish blue | 0.211, 0.175 | Blue | Blue | Blue |
| 9 | 2.5 R 5/10 | Moderate red | 0.453, 0.306 | Dark Orange | Dark Orange | Salmon |
| 10 | 5 P 3/7 | Purple | 0.285, 0.202 | Dark Blue | Dark Purple | Purple |
| 11 | 5 GY 7.1/9.1 | Yellow green | 0.380, 0.489 | Dark Yellow | Dark Yellow | Lime Green |
| 12 | 10 YR 7/10.5 | Orange Yellow | 0.473, 0.438 | Yellow | Yellow | Yellow-Orange |
| Row 3: Primary Colors | | | | | | |
| 13 | 7.5 PB 2.9/12.7 | Blue | 0.187, 0.129 | Dark Blue | Dark Blue | Dark Blue |
| 14 | 0.1 G 5.4/9.6 | Green | 0.305, 0.478 | Brown | Greenish Brown | Green |
| 15 | 5 R 4/12 | Red | 0.539, 0.313 | Dark Brown | Reddish Brown | Red |
| 16 | 5 Y 8/11.1 | Yellow | 0.448, 0.470 | Yellow | Yellow | Yellow |
| 17 | 2.5 RP 5/12 | Magenta | 0.364, 0.233 | Light Blue | Light Purplish Blue | Light Magenta |
| 18 | 5 B 5/8 | Cyan | 0.196, 0.252 | Blue | Blue | Blue |
| Row 4: Grayscale Colors | | | | | | |
| 19 | N 9.5/ | White | 0.310, 0.316 | White | White | White |
| 20 | N 8/ | Neutral 8 | 0.310, 0.316 | Light Gray | Light Gray | Light Gray |
| 21 | N 6.5/ | Neutral 6.5 | 0.310, 0.316 | Medium Gray | Medium Gray | Medium Gray |
| 22 | N 5/ | Neutral 5 | 0.310, 0.316 | Gray | Gray | Gray |
| 23 | N 3.5/ | Neutral 3.5 | 0.310, 0.316 | Dark Gray | Dark Gray | Dark Gray |
| 24 | N 2/ | Black | 0.310, 0.316 | Black | Black | Black |

*FIG. 7*

LIGHTING SYSTEM FOR SIMULATING CONDITIONS OF COLOR DEFICIENT VISION AND DEMONSTRATING EFFECTIVENESS OF COLOR-BLINDNESS COMPENSATING EYEWEAR

CROSS REFERENCE TO RELATED APPLICATIONS

This application claims benefit of priority to U.S. Provisional Patent Application No. 62/405,467 titled "Lighting System For Simulating Conditions of Color Deficient Vision and Demonstrating Effectiveness of Color Blindness Compensating Eyewear" filed Oct. 7, 2016, which is incorporated herein by reference in its entirety.

This application is also related to PCT Patent Application No. PCT/US2012/027790 titled "Multi-Band Color Vision Filters and Method by LP-Optimization" filed Mar. 5, 2012, to U.S. patent application Ser. No. 14/014,991 titled "Multi-Band Color Vision Filters and Method by LP-Optimization" filed Aug. 30, 2013, and to PCT Patent Application No. PCT/US16/21399 titled "Optical Filters Affecting Color Vision in a Desired Manner and Design Method Thereof by Non-Linear Optimization" filed Mar. 8, 2016, each of which is incorporated herein by reference in its entirety.

FIELD OF THE INVENTION

The invention generally relates to apparatus that emit substantially white light for projection of images and/or illumination of objects for viewing by humans and/or color cameras, such as lamps, lamp assemblies, flashlights and projectors. The invention also generally relates to design of the spectral power distribution of light sources to produce a desired quality of color rendering. The invention also generally relates to the use of narrow-band spectral filters in ophthalmic systems to ameliorate symptoms of color vision deficiency and color blindness. The invention also generally relates to methods and apparatus that exaggerate, demonstrate or make visible a functional optical feature that is not readily observed by ordinary visual inspection of an ophthalmic lens or optical apparatus incorporating a functional optical feature.

REFERENCES

Andrew Stockman and Lindsay T. Sharpe. The spectral sensitivities of the middle and long-wavelength-sensitive cones derived from measurements in observers of known genotype. Vision Research, 40(13):1711-1737, 2000.

Günter Wyszecki and W. S. Stiles. Color Science: Concepts and Methods, Quantitative Data and Formulae. ISBN #0471021067 in The Wiley series in pure and applied optics. Wiley, 1982.

Parkkinen J. P. S., Hallikainen J. and Jaaskelainen T. "Characteristic spectra of Munsell colors". Journal of the Optical Society of America A, 6, no. 2, 1989, pp. 318-322.

Munsell Color Corporation: The Munsell Book of Color, Glossy Edition. ISBN #9994678620. 1980.

C. S. McCamy, H. Marcus, and J. G. Davidson (1976). "A Color-Rendition Chart". Journal of Applied Photographic Engineering 2(3). 95-99.

Dictionary of Optometry and Visual Science, 7th Edition, Michel Millodot. ISBN-9780702051883, Ebook, Release Date: 2008

BACKGROUND

Artificial sources of white light illumination are devices that emit substantially white light by which humans may perform tasks that depend on photopic trichromatic color vision. Light is considered by human observers to be substantially white if its color lies on or near the blackbody radiation curve, which includes a range of light colors from yellow through bluish white. The spectral power distribution of light emitted by an illuminant may be designed according to requirements such as providing a desired quality of color rendering, or such as providing a desired level of luminous efficiency (e.g. as measured in terms of lumens per watt). For persons with substantially normal color vision, the experience of color blind people in the natural world is not readily understood. Apparatus that demonstrate the experience of a disability are useful for increasing awareness and appreciation of the conditions caused by that disability in persons who lack direct experience. Optical filters having narrow-band spectral transmittance characteristics may be incorporated into ophthalmic lenses that are used to ameliorate the symptoms of color vision deficiency. The utility of an ophthalmic lens that ameliorates the symptoms of color vision deficiency cannot be directly experienced by a person without color vision deficiency. Devices that demonstrate the functionalized properties of ophthalmic lenses are useful in retail sales as visual aids to explain and demonstrate the benefits of ophthalmic lens products to prospective customers, to dispensing opticians and doctors, and to the general public.

SUMMARY

Disclosed herein are apparatus that provide illumination to a visual scene, such as lamps, lighting fixture assemblies, portable flashlights, or any similar device that provides a source of light enabling photopic color vision. Also disclosed are the spectral power distributions of lights that enable the simulation of color deficient vision to persons with substantially normal color vision. Also disclosed are descriptions of embodiments of light sources having said spectral power distributions. Persons with substantially normal color vision includes persons with normal color vision as well as persons with mild or moderate color vision deficiency. Color vision deficiency includes protanomaly, deuteranomaly, tritanomaly, protanopia, deuteranopia, tritanopia, red-green color blindness, blue-green color blindness, achromatopsia, incomplete achromatopsia, dyschromatopsia, acquired color vision deficiency, S-cone monochromacy, rod-monochromacy, and general loss of chromatic sensitivity. Also disclosed herein are methods for employing the illumination apparatus to demonstrate the effectiveness of certain ophthalmic lenses, wherein the lenses use narrow-band spectral transmission features designed to improve the color vision of persons with color vision deficiency.

The teachings, methods and embodiments disclosed herein may be used to define manufacturing requirements and specifications to manufacture devices that provide the desired effect on color vision and/or desired interaction with color vision-modifying ophthalmic lenses. Suitable light-generating technologies providing the desired effects include light emitting diodes (LEDs), fluorescent lamps, low-pressure sodium lamps, high pressure sodium lamps, arc lamps, filament lamps, quantum dot emitters, visible lasers, and any combination of these technologies. The light emitted by one or more light-generating technologies may be further modified by means of optical filtering to achieve the desired effect on color vision. Optical filtering means include absorptive optical filters, narrow-band absorptive optical filters, broad-band absorptive optical filters, polarization filters, wavelength-selective quarter-wave retarder stack filters, diffraction gratings, fluorescent wavelength-shifting films, dielectric multi-layer wavelength-selective mirrors, and suitable combinations thereof. Any suitable means of combining the light emitting technologies with the optical filter technologies may be performed to result in a satisfactory illumination apparatus, for example by incorporating a variety of suitable light emitting technologies and filters into an enclosure and providing adequate diffusion of the emitted light to create a substantially white illuminant with a substantially spatially-homogeneous spectral radiant flux.

An ophthalmic lens is a lens for use with an eye. An ophthalmic lens may provide optical (focusing) correction to the eye, or it may be of zero power and provide no such correction. Eyeglass lenses (e.g., clear or substantially transparent lenses), tinted or colored lenses, sunglass lenses, polarized lenses, gradient lenses, photochromic lenses, multi-focal (e.g. progressive, bifocal and trifocal) lenses and contact lenses are examples of ophthalmic lenses.

Ophthalmic lenses are a type of optical aperture. Generally, optical apertures include other optical elements such as windows, films, scopes, etc. An optical aperture may be functionalized by the incorporation of an optical material causing a wavelength-selective attenuation of the spectral power density of light transmitted by the aperture. Herein, the unqualified use of the term "filter" shall be understood to refer to an optical aperture that has a spectral transmittance function, unless otherwise specified.

Transmittance of a filter is the fraction of light that passes through the filter at a particular wavelength. The transmittance may be stated as a ratio, e.g. 0.40, or as a percent, e.g. 40%. The visible wavelengths of light are between about 390 nanometers and about 750 nanometers, however it is also reasonable to consider only wavelengths between 400 nanometers and about 700 nanometers, or between 420 nanometers and about 670 nanometers, or between 450 nanometers and 650 nanometers, because the human eye is relatively insensitive to light at the limits of the spectral sensitivity window, therefore the properties of filters over between 390 nanometers to 450 nanometers and between 650 nanometers and 750 nanometers are imperceptible, or nearly imperceptible, to human color vision. The transmittance spectrum of a filter refers to its transmission across the visible spectrum of light, unless otherwise specified herein. The transmittance spectra of filters may be quantified by tabulating the transmittance per wavelength, using a wavelength step size of 1 nanometer, for example, or using any other reasonable step size or other sampling method that achieves a spectral resolution of 10 nanometers or smaller.

A spectral power density function (which may represent the transmittance, emittance, reflectance or generally any measurable spectral property of an optical filter), may be described as having broad-band characteristics at one or more locations in the wavelength spectrum, or as having narrow-band characteristics at one or more locations, or as having both broad and narrow-band characteristics. A broad-band spectral characteristic is defined herein as a peak or notch in the spectral power spectrum having a full-width-half-maximum width greater than or equal to forty (40) nanometers around its wavelength of maximum transmission (for filters), or of maximum absorption (for filters), or of maximum emission (for illuminants) or of minimum emission (for illuminants). A narrow-band spectral characteristic is defined herein as a peak or notch in the spectral power spectrum having a full-width-half-maximum less than forty (40) nanometers around its wavelength of maximum transmission (for filters), or of maximum absorption (for filters), or of maximum emission (for illuminants) or of minimum emission (for illuminants).

The distinction between broad versus narrow as described above is based on the sensitivity of a typical trichromatic imaging system such as human color vision, or a three-color camera sensor. Trichromatic imaging systems generally partition the visible spectrum into three broad spectral bands, and are therefore "blind" to certain spectral features which are sufficiently narrow. Such narrow-band features are generally not readily observable by casual visual inspection. An optical apparatus comprising narrow-band features may have a general color appearance (for example the average color of light emitted by, or transmitted by the apparatus), and that color may appear to be the same as the general color appearance of another optical apparatus comprising only broad-band features. The property of lights that have different spectral composition but the same color appearance is called metamerism in color vision science. Mathematically metamerism is explained by describing a trichromatic image sensing as a linear projection from infinite dimensional Hilbert space into a three-dimensional color space.

The definition of broad versus narrow features as given herein is generally useful to demarcate properties of optical apparatus designed to achieve particular transformative functions on the spectral content of light, where said functions are generally only possible by use of optical components enabling narrow-band spectral features.

With respect to absorptive optical materials comprising one or more dyes or dye-like absorptive materials, these materials may be described as broad-band dyes, or as narrow band dyes. The term standard dyes used herein shall refer to dyes having broad-band characteristics and not having narrow-band characteristics. Some materials such as neodymium oxide may comprise narrow band absorptive features at one or more locations in the visible spectrum, in addition to broad band absorptive characteristics.

The mean transmittance of a filter is the average transmittance over a contiguous range of wavelengths, for example, the mean transmittance between 500 nanometers and 599 nanometers may be calculated by summing the transmittance at each wavelength within the range using a step size of 1 nanometer, and then dividing the sum by 100.

The mean spectral radiance of an illuminant is the average radiant flux over a contiguous range of wavelengths, for example, the mean spectral radiance between 500 nanometers and 599 nanometers may be calculated by summing the radiant flux at each wavelength within the range using a step size of 1 nanometer, and then dividing the sum by 100.

The luminous transmittance of a filter is the weighted average transmittance of the filter across the visible spectrum, where the weighting function is a photopic luminous efficiency function. A photopic luminous efficiency function defines the relative brightness of monochromatic light, wherein monochromatic light is a light source defined as radiating photons having a singular wavelength. Photopic luminous efficiency functions are defined according to standard observer models, for example according to the CIE 1932 2-degree Standard Observer.

The luminous flux (lumens) of an illuminant is the total quantity of luminous flux emitted by an illuminant. The luminous flux is related to the radiant flux by weighting each wavelength of the radiant flux according to its apparent brightness as defined by a photopic luminous efficiency function. A photopic luminous efficiency function defines the relative brightness of monochromatic light, wherein monochromatic light is a light source defined as radiating photons with only one wavelength. Photopic luminous efficiency functions are defined according to standard observer models, for example according to the CIE 1932 2-degree Standard Observer. Lux is the measurement of luminous flux per unit area, wherein 1 lux is equal to 1 lumen per square meter. Normal trichromatic human color vision generally operates between 20 (twenty) lux and 20,000 (twenty thousand) lux.

The white-point of a filter is the (x,y) chromaticity coordinates of average daylight as seen through the filter, where average daylight is defined as Standard Illuminant D65 and the (x,y) chromaticity coordinates are calculated according to the CIE 1932 2-degree Standard Observer and the CIE Yxy color space, unless otherwise specified.

The white-point of an illuminant is the (x,y) chromaticity coordinates of the light emitted by the illuminant, where the (x,y) chromaticity coordinates are calculated according to the CIE 1932 2-degree Standard Observer and the CIE Yxy color space, unless otherwise specified.

The correlated color temperature of a filter is the temperature corresponding to a point on the black-body locus nearest to the white-point of the filter.

The correlated color temperature of an illuminant is the temperature corresponding to a point on the black-body locus nearest to the white-point of the illuminant.

A neutral density filter is a filter that has substantially uniform transmittance across the visible spectrum. Neutral density filters are referred to by the letters "ND" followed by numbers, where the numbers indicate the percent transmission provided by the filter. For example, an ND25 filter has approximately a 25 (twenty five) percent transmittance over the visible spectrum. The white-point of a neutral density filter with respect to any illuminant as seen through the filter is substantially the same as the white-point of the illuminant. Therefore, an ND25 filter attenuates light by a factor of 4 without changing the color of transmitted light.

Measurement of the transmittance spectrum of an ophthalmic system may be performed according to a suitable method for measurement of the spectral properties of ophthalmic lenses, for example by averaging the measurement over a region of the lens corresponding to at least a 10-degree field of view, when the ophthalmic system is used to filter light received by the eye in a typical fashion. For example, the spectral measurement may be performed by passing a reference light through an area on an eyeglass lens having a diameter between about 5 millimeters and about 20 millimeters at the center of the lens, and then performing a spectral analysis on the light transformed by the ophthalmic system. The optical filtering material may be incorporated into the entire body of an ophthalmic lens, or into a segment of the lens, or may be applied with a gradient of increasing density across the surface of the lens. A similar measurement on a contact lens would use a smaller area that is appropriately chosen and proportional to diameter of the lens. Optical filtering materials may be incorporated into the entire body of a contact lens, or may be confined to only the area covering the pupil.

If an optical filter is incorporated into an ophthalmic lens, then its properties may be measured according to industry-standard conventions and definitions, for example, the calculations just described are defined with respect to eyewear by American National Standards Institute Z80.3-2010 section 4.6 (transmittance), section 4.6.1 (luminous transmittance), section 4.6.2 (mean transmittance), and section 4.6.3.1 (white-point/chromaticity coordinates of average daylight). Similar calculations for contact lenses are defined by ANSI Z80.20-2010, for intraocular lenses by ANSI Z80.7-2002, and for ski and snow goggles by ASTM F659-12.

Measurement of the transmittance spectra of filters integrated into a lamp assembly may comprise measuring the spectral radiance of light emitted by the lamp assembly when the filter is removed, and then measuring the relative spectral radiance of light when the filter is placed into the path of the output beam. The measurement may also be performed by sampling and averaging the spectral radiance at multiple locations within the output beam. Any reasonable method of measuring the spectral response of a filter integrated into a system may be used.

Measurement of the spectral radiant flux of illuminants may be performed according to a suitable method for measurement of the spectral properties of illuminants, for example by dispersing the light into an integrating sphere measuring the spectral radiant flux with a spectrophotometer at one or more points around the sphere. Alternatively, the spectral radiant flux may be measured with a spectrophotometer by sampling the light at a point within the output beam, for example at the point of peak intensity in the illuminant's output beam or output cone of radiation. Any reasonable method of measuring the spectral radiant flux of an illuminant may be used. The absolute radiant flux may be calculated by comparing a spectrophotometric measurement to the measurement obtained from a calibrated light source of known spectral radiance. The lux (lumens per square meter) may be measured using a lux meter placed within the output beam at an appropriate position where an object under illumination is viewed or on a projection surface.

Measurement of the color rendering index (CRI) of an illuminant may be performed according to the methods defined by the International Commission on Illumination as described in CIE (1999), Colour rendering (TC 1-33 closing remarks), Publication 135/2, Vienna: CIE Central Bureau, ISBN 3-900734-97-6.

In one embodiment, an illuminant comprises at least two light emitters: the first emitter comprising substantially white light having a CRI of at least 70, and the second emitter having a substantially yellow-colored light characterized by a narrow-band spectral feature with a center wavelength between 570 nanometers and 600 nanometers, and a band-width of between 1 nanometers and 40 nanometers.

In one variation, the illuminant has a control system capable of adjusting the relative luminous flux of the first emitter relative to the second emitter.

In another variation, the illuminant comprises at least three light emitters: the first emitter comprising substantially white light having a CRI of at least 80, the second emitter having substantially yellow-colored light characterized by a narrow-band spectral feature with a center wavelength between 570 nanometers and 600 nanometers, and a band-width of between 1 nanometers and 40 nanometers, and the third emitter comprising a substantially blue-colored light having a wavelength of maximum emission between 440 nanometers to 490 nanometers and a spectral bandwidth of between 1 nanometers to 60 nanometers centered around the wavelength of maximum emission.

In another variation, the illuminant has a control system capable of adjusting the relative luminous flux of the first emitter relative to the combined second and third emitters.

In another variation, the luminous flux of the yellow-colored emitter is at least five times greater than the luminous flux of the white emitter. In another variation the relative luminous flux is at least ten times greater.

In another variation the illuminant comprises a control system capable of adjusting the relative luminous flux so that the luminous flux of the white emitter can be adjusted between 20% and 150% of the luminous flux of the yellow emitter. In another variation the range of adjustment comprises 10% to 300%.

In another embodiment, a system for demonstrating an optical filter designed to ameliorate the effects of color vision deficiency comprises an assembly or system comprising an illuminant having the properties of any of the illuminant embodiments referenced above, a colorful object under illumination by the illuminant, an aperture by which the illuminated object is visible with respect to a reference filter, and a second aperture by which the object is visible through a trial filter. The trial filter comprises a narrow-band spectral transmission feature that is complementary to a narrow-band spectral emission feature of the illuminant. Preferably the reference filter is the null filter, or is a neutral density filter, or comprises only broad-band spectral transmittance features. In some aspects the filters are incorporated into windows, or into segments upon a window, through which the illuminated object can be readily viewed by an observer situated in proximity to the apparatus. In some aspects the apparatus may have the form of a kiosk.

In another embodiment, a method for demonstrating the difference between color deficient vision versus normal color vision comprises configuring an illuminant comprising a yellow emitter and a white emitter so that the luminous flux of the yellow emitter is at least five times greater than the luminous flux of the white emitter, viewing a colorful object or item under the illuminant, and then using a control system to adjust the relative luminous flux of the emitters so that the luminous flux of the yellow emitter is at most two times greater than the luminous flux of the white emitter. The illuminant may have the properties of any of the illuminant embodiments referenced above, for example.

In another embodiment, a method for demonstrating an ophthalmic lens designed to ameliorate the effects of color vision deficiency comprises configuring an illuminant comprising a yellow emitter and a white emitter so that the luminous flux of the yellow emitter is at least five times greater than the luminous flux of the white emitter, viewing a colorful object or item under the illuminant, and then viewing the same object as seen through an ophthalmic lens wherein the ophthalmic lens comprises at a spectral transmittance with a narrow-band feature characterized by a narrow-band absorptive notch having a wavelength of maximum absorption between 570 nanometers and 600 nanometers, and the mean spectral transmittance over a spectral band 20 nanometers wide centered at the wavelength of maximum absorption is less than one half of the luminous transmittance of the ophthalmic lens. The illuminant may have the properties of any of the illuminant embodiments referenced above, for example.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 7 is a table of the color names according to a normal observer from a standard color checker as viewed under an illuminant that simulates color vision deficiency, and the color names given by a normal observer viewing the same color checker through an ophthalmic lens designed to compensate for the symptoms of common red-green color blindness.

DETAILED DESCRIPTION

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used in this specification and the appended claims, the singular forms "a," "an," and "the" include plural referents unless the context clearly indicates otherwise.

The spectral characteristics and quality of light emitted by illuminants may be designed or configured to optimize the performance of the illuminant with respect to a desired function, for example by optimizing the lumens per watt of the illuminant (power efficiency), or its color rendering index (CRI) or according to any desired relative weighting of luminous efficiency versus CRI. Lights with a high CRI (for example having a CRI of at least 80 and more preferably at least 90) generate light that causes objects to appear with accurate coloration that is reasonably equivalent to standard daylight. As described herein, a light with unusually low color rendering index may also provide utility as a simulation of color vision deficiency (also called color blindness). An illuminant that is capable of simulating the conditions of color vision deficiency is useful for demonstrating the effects of color blindness to persons with substantially normal color vision. Furthermore, the functional properties of ophthalmic lenses or other optical apertures (such as windows) containing narrow-band spectral transmission features can be demonstrated in combination with illuminants comprising complementary narrow-band spectral emission features so that the ability of persons to understand and appreciate the spectral functional properties of the optical aperture is facilitated.

Under ordinary inspection with white light having a high CRI (e.g. of at least 80), ophthalmic lenses comprising narrow-band spectral transmittance features appear to be indistinguishable from ordinary tinted lenses that are formed having only broad-band spectral transmittance characteristics. This condition is known as metamerism, wherein a plurality of distinct spectral lights may appear the same to the human eye. The human eye reduces the infinite dimensional space of spectral power distributions to a three dimensional space of trichromatic color vision, and therefore is blind to different members of the equivalence class of spectra corresponding to a color appearance. The dimensionality of the design space of ophthalmic filters comprising narrow-band spectral features may comprise more than three dimensional components. For example, a filter may comprise a mixture of five distinct narrow-band dyes. The greater dimensionality of the design space (i.e. mixtures of five dyes) exceeds the dimensionality of the human eye (i.e. three classes of retinal cone photopigments), therefore optical filters with differing spectral transmittance properties can appear to have the same color to the human eye when viewed with respect to broad-band lights, for example under a white light having a CRI of at least 80 and against a white background. In conventional color science, a goal in the design of pigment systems such as for print reproduction is to reduce the admission of metamerism, so that colors appear maximally stable under a range of illumination types such as between fluorescent lamps versus daylight. With respect to the design of ophthalmic filters comprising narrow-band features, the filters may be designed to intentionally disrupt perceived metamerism for a human observer. An example system for exaggerating the effects of metameric disruption by a narrow-band filter comprises combining a narrow-band filter with a narrow-band light emitter. This system is useful as an educational aid, and to facilitate the selection and sale of lens products in a retail environment.

Figure 1:
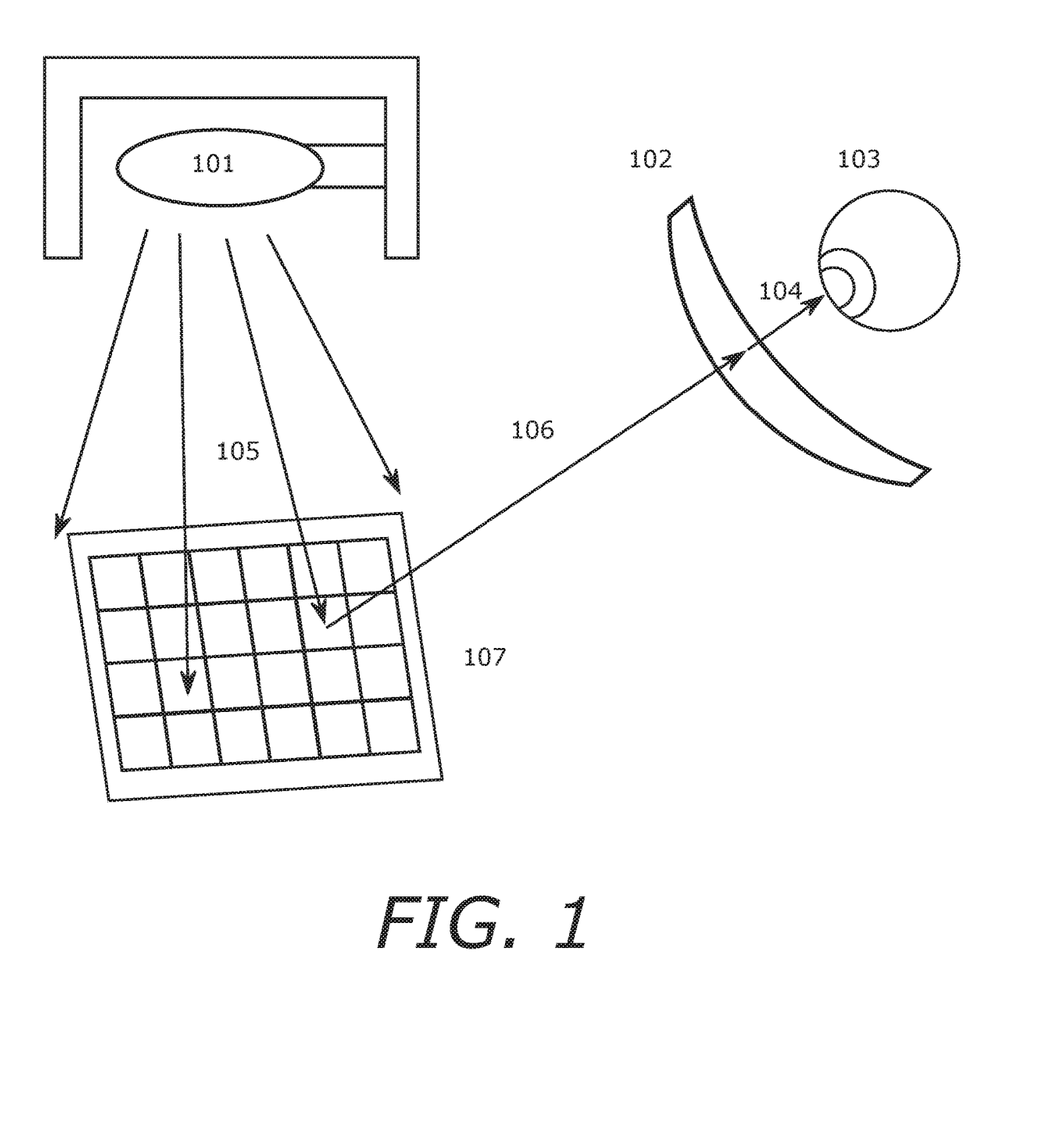
FIG. 1 schematically depicts an example use of an illuminant to demonstrate spectral filtering properties of a lens. The spectral radiant flux of the illuminant has an emission peak in the yellow band of the visible spectrum, and the lens has a narrow-band transmission notch located in the yellow band of the visible spectrum.

An example method and example apparatus for demonstrating the effect of an ophthalmic lens comprising a narrow-band spectral transmittance feature is depicted graphically in FIG. 1. This figures shows an illuminant 101, the ophthalmic lens 102 (also referred to herein as the "trial filter"), light emitted by the illuminant 105 and incident on a colorful object 107, and radiant colored light 106 reflected from the object and filtered by the ophthalmic lens 102, which transforms the reflected colored light 106 to colored light 104 received by the eye of an observer 103. In this method and apparatus the ophthalmic lens is configured jointly with the spectral radiant flux of the illuminant so that there is a large and readily seen change in apparent colors of the object as seen through the lens as compared to the colors of the object as seen without the intervening trial lens. An example of the spectral power distribution radiated by the illuminant is described below with reference to FIG. 4. Examples of the spectral transmittance of ophthalmic lenses designed to produce a desired effect of compensating for symptoms of color vision deficiency are described below with reference to FIG. 5 and FIG. 6. The spectral features of the illuminant and of the ophthalmic lens may be configured so that compared to viewing the colorful object under illumination with the naked eye, the appearance of colors may be altered when viewed through the lens to produce a substantially different color appearance of the object. In one example, when the colorful object is viewed directly (without the intervening lens), red and green colors on the object appear identical or nearly identical. In contrast, when the colorful object under the same illumination is viewed through the intervening trial lens, the similarity between the colors may be substantially or entirely removed, for example by causing the red and green colors that previously appeared nearly identical to become clearly differentiated as vividly red and green colors. This method and apparatus are useful for demonstrating to an individual with substantially normal color vision how the trial lens is effective at compensating for the symptoms of color vision deficiency. For example, persons with red-green color blindness (also called deuteranomaly, deuteranopia, protanomaly or protanopia) may see red and green colors as similar or nearly identical, and the trial lens provides a functional benefit to such persons by improving the apparent differences between red and green colors while simultaneously not impairing the apparent color accuracy of other colors such as blue, yellow and white.

Figure 2:
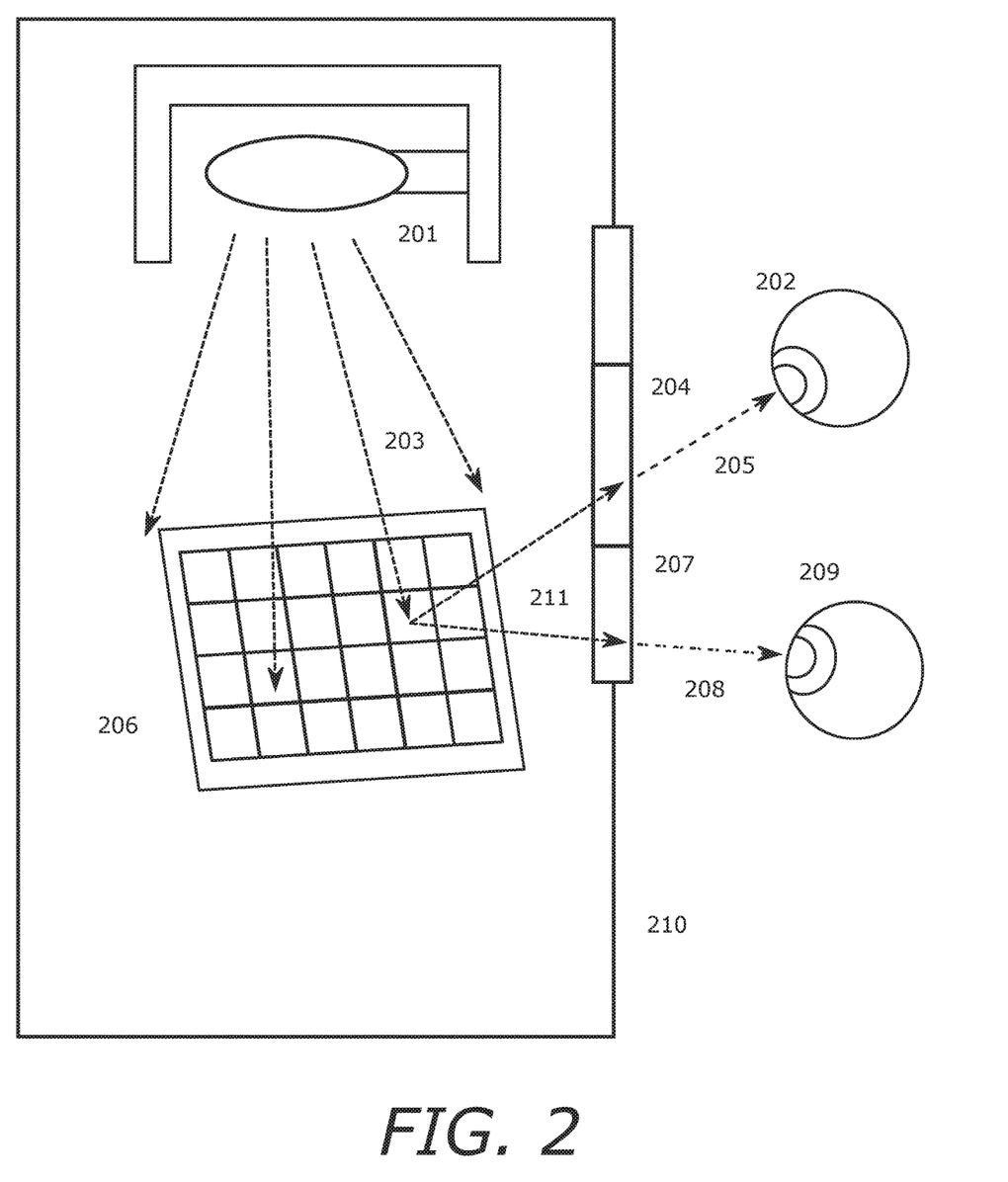
FIG. 2 schematically depicts an example kiosk apparatus incorporating a trial filter window and a reference filter window.

In another embodiment, an example method and example apparatus for demonstrating the effect of an optical window comprising a narrow-band spectral transmittance feature is depicted graphically in FIG. 2. This figure shows an illuminant 201, a trial optical window 204, and a reference optical window 207. The windows are configured using an enclosure or frame 210 within which light radiated by an illuminant 203 is incident onto a colorful object 206, causing colored reflected light 211 to be transmitted through the trial window 204 and the reference window 207 resulting in a first transmitted image 205 received by a first observer 202 and a second transmitted image 208 received by a second observer 209. The reference optical window may comprise, for example, a neutral density filter and the trial optical window may comprise the narrow-band spectral transmittance feature. Depending on the position of an observer (e.g. at the first position 202 or second position 209) the view of the object is filtered by either the trial window, or by the reference window. The two windows may appear to have the same color of tint (i.e. are metameric). However, by observing the illuminated object from different vantage points, the observer is able to appreciate the functional difference on color vision caused by the window comprising a narrow-band spectral transmittance feature. The narrow-band spectral transmittance feature of the window may be jointly configured with the spectral power distribution of the illuminant to exaggerate or enhance the effect on color vision. An example of a spectral power distribution radiated by the illuminant is described in below with reference to FIG. 4. Examples of the spectral transmittance of optical filters designed to produce a desired effect of compensating for symptoms of color vision deficiency are described below with reference to FIG. 5 and FIG. 6. The optical filters are capable of being incorporated into an optical window.

The method and apparatus depicted in FIG. 2 enables demonstration of the narrow-band functional features of a trial filter incorporated into the first optical window in comparison to the broad-band functional features of a reference filter incorporated into the second optical window, without requiring the observer to use eyewear, or to otherwise use or hold an object (such as a lorgnette) incorporating an optical lens or window. For example, the apparatus may be a free-standing kiosk that is placed in a retail shopping environment, or in a museum, or other public space.

In some embodiments of the method and apparatus depicted in FIG. 1 and in FIG. 2, the illuminant may comprise a combination of multiple light emitters having different spectral power distributions. In some embodiments the method and apparatus may also comprise a control system that is capable of modulating the relative luminous flux of the multiple emitters. The control system may be used to interactively demonstrate different visual conditions, for example by providing a knob or slider by which an operator can change the relative luminous flux of the emitters in real time. The control system may also modulate the relative luminous flux automatically, for example by following a programmed sequence.

Figure 3:
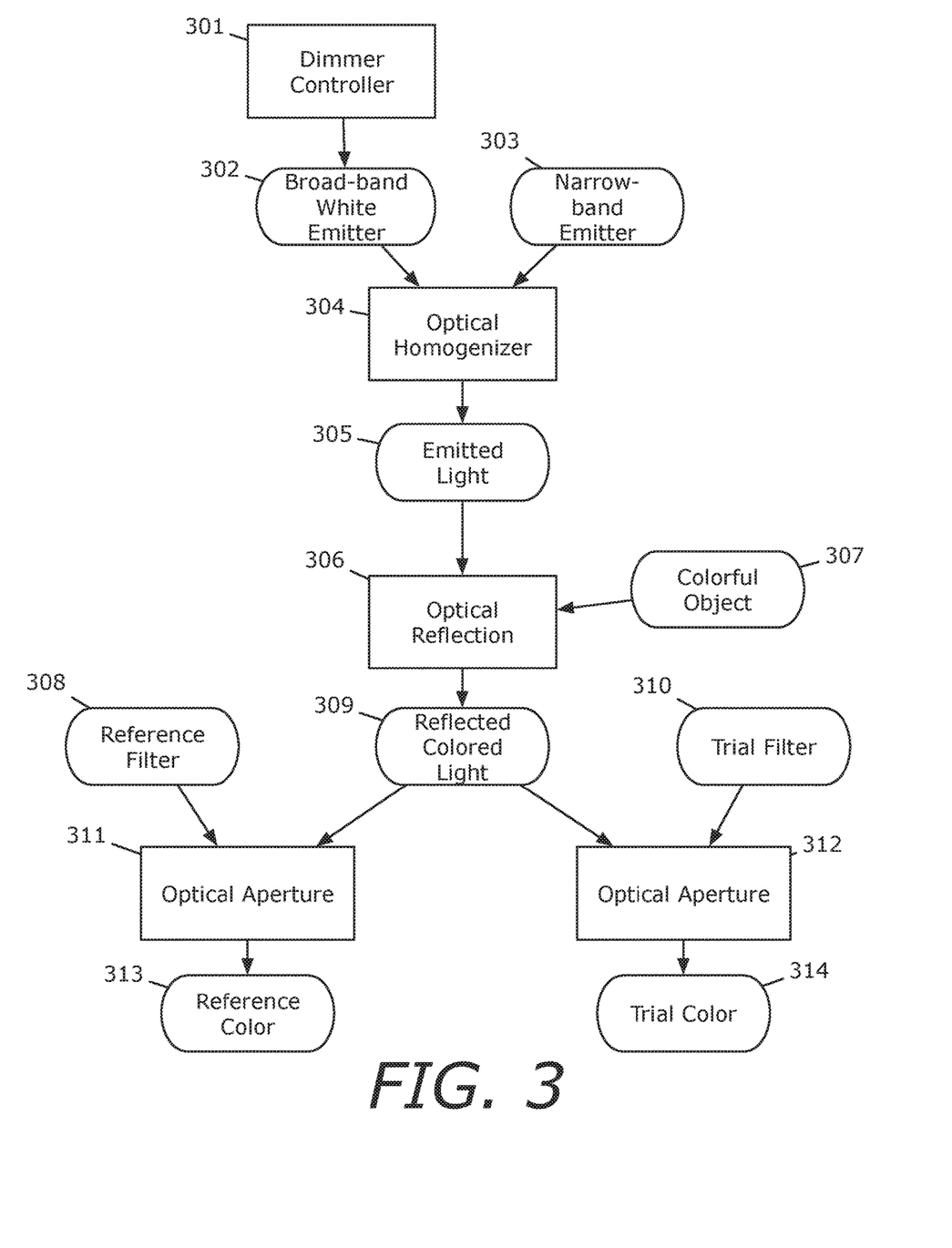
FIG. 3 depicts the organization of an example illuminant system comprising a plurality of emitters and control systems for modulating the relative luminous flux of the emitters.

The operation of a method and apparatus as depicted in FIG. 1 and FIG. 2 is graphically depicted in the flow chart of FIG. 3. In this flow chart, an illuminant radiating light comprises elements numbered 301 through 305 (dimmer controller 301, broad-band white emitter 302, narrow band emitter 303, optical homogenizer 304, and emitted light 305). A system of optical interactions (e.g. reflection and transmission) comprises elements 306-312 (optical reflection 306, colorful object 307, reference filter 308, reflected colored light 309, trial filter 310, optical aperture 311, and optical aperture 312) resulting in two different color sensations 313 and 314 corresponding to the view of colorful object 307 as seen through trial filter 310 as compared to the view of colorful object 307 as seen through the reference filter 308. The reference filter may have broad-band spectral transmittance features, for example it may be a neutral density filter having equal luminous transmittance to the trial filter. The reference filter may also be a pass-through filter, such as a clear window or "unfiltered" condition. The trial filter may comprise one or more narrow-band spectral transmittance features. For example the trial filter may comprise a narrow-band spectral absorptance peak located between 570 and 600 nanometers. The reference filter and the trial filter may each be incorporated into some type of optical aperture 311 and 312, for example an ophthalmic lens or a window. The illuminant assembly 301 through 306 may comprise multiple types of light emitters, for example it may comprise a broad-band emitter that outputs white light 302, and a narrow-band emitter 303. The narrow-band emitter may be selected so that the spectral flux of the emitter is attenuated by the narrow-band absorptance feature of the trial filter, and the attenuation of the narrow-band emitted light is greater than the attenuation of the broad-band emitted light. For example, the attenuation may be at least 50% greater, or may be at least 200% greater.

Figure 4:
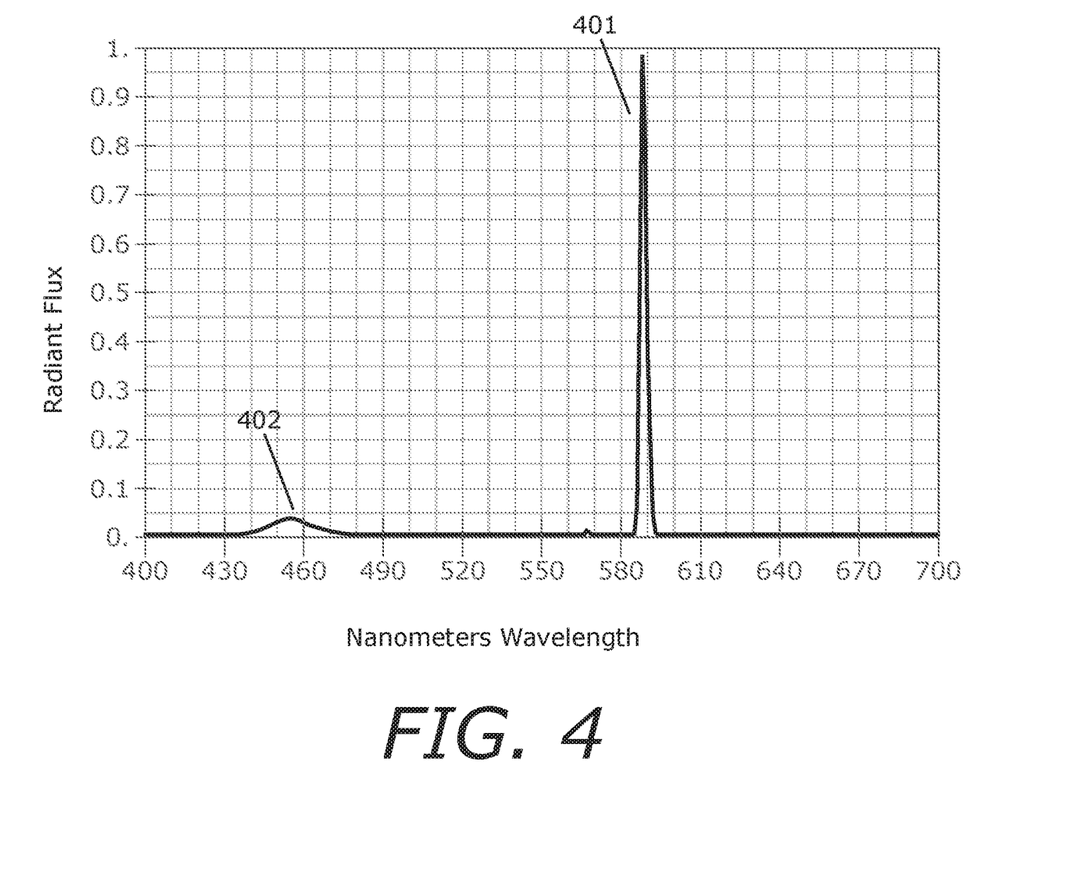
FIG. 4 is a graphical plot of the spectral power distribution of an example illuminant comprising a plurality of emitters.

The graph of FIG. 4 depicts the spectral radiant flux of an example illuminant designed to work with the methods of the present disclosure. A narrow-band spectral feature at 401 comprises a spectral emission peak centered at about 589 nanometers and having a half-maximum width of less than or equal to 5 nanometers. This spectral feature is characteristic of the output of a low pressure sodium (LPS) gas-discharge tube. The color of LPS lamps is generally described as being yellow. A second narrow-band spectral feature at 402 corresponds to the emission profile of blue LEDs, centered at about 455 nanometers and having a half-maximum width of about 40 nanometers.

Figure 5:
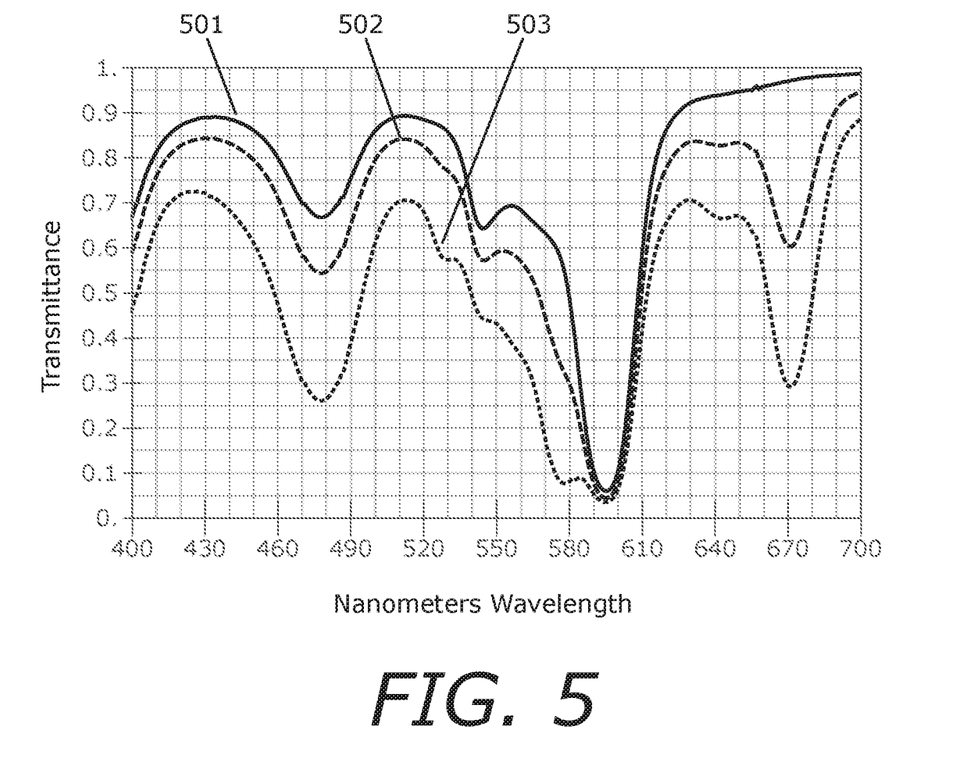
FIG. 5 is a graphical plot of the spectral transmittance of example filters designed to compensate for the symptoms of color vision deficiency.

The graph of FIG. 5 depicts the spectral transmittance of a series of example filtering lenses that may be used in conjunction with the lighting systems described herein to achieve the desired effect on color vision. The graph at 501 corresponds to the transmittance of a commercially available lens under the brand name EnChroma Cx-65. The transmission spectrum of this lens comprises a narrow-band spectral transmittance feature centered at 595 nanometers with a half-minimum width of about 25 nanometers. The graph at 502 corresponds to the transmittance of an experimental lens featuring an increased concentration of the narrow-band absorbing dyes comprised by the first lens. The graph at 503 corresponds to the transmittance of an experimental lens featuring a further increased concentration of the narrow-band absorbing dyes, and the addition of a third dye component with a maximum absorption at about 575 nanometers, causing a broadening of the absorptive notch feature located between 580 nanometers to 590 nanometers.

Figure 6:
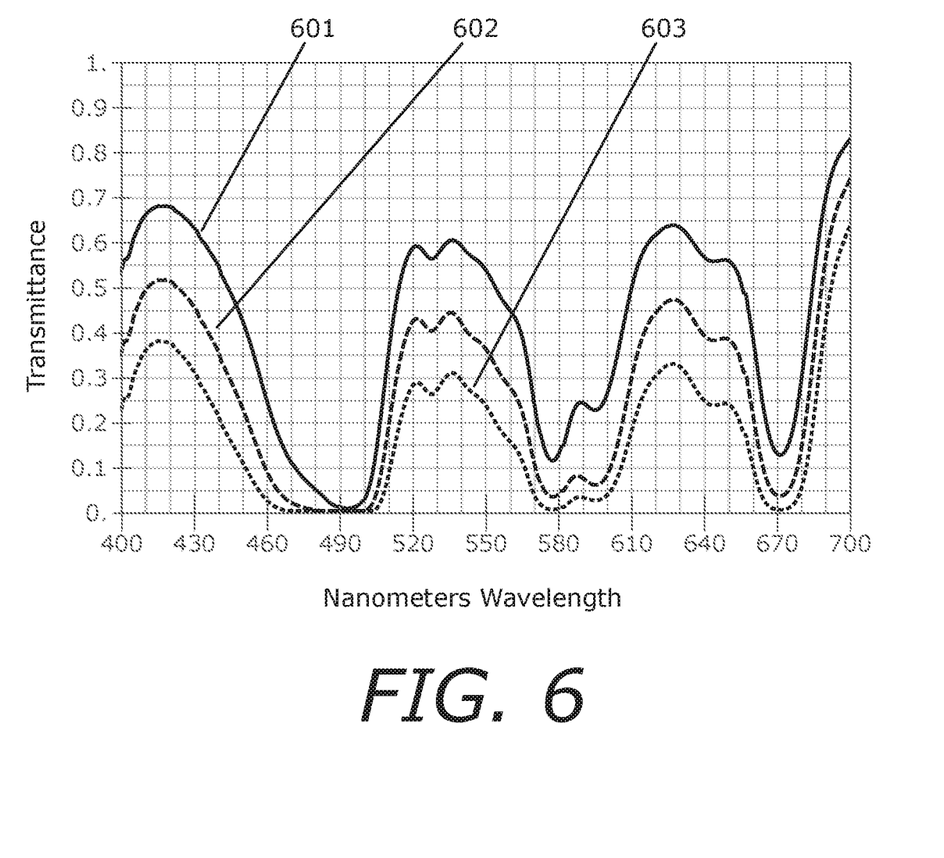
FIG. 6 is a graphical plot of the spectral transmittance of another example filter designed to compensate for the symptoms of color vision deficiency.

The graph of FIG. 6 depicts the spectral transmittance of another series of example filtering lenses that may be used in conjunction with the lighting systems described herein to achieve the desired effect on color vision. The graph at 603 corresponds to the transmittance of a commercially available lens under the brand name EnChroma Cx-14. The graph at 602 corresponds to the transmittance of a commercially available lens under the brand name EnChroma Cx-25. The graph at 601 corresponds to the transmittance of an experimental lens comprising a reduced concentration of narrow-band absorbing dyes but in a similar ratio as in the EnChroma Cx-14 and EnChroma Cx-25. All three spectral transmittance curves (601, 602, 603) comprise at least a narrow-band spectral transmittance feature located between 580 nanometers and 590 nanometers having a half-minimum width of less than 40 nanometers.

In a first example, an illuminant was constructed comprising a narrow-band yellow emitter comprising of two 55-Watt high-intensity low pressure sodium bulbs, commercially available under the product name SOX 90W BY22d 1SL/12 made by Philips Lighting Holding B.V., a broad-band white emitter comprising a 100 Watt series of white-light emitting LED modules commercially available under the brand name BC Series High CRI MCPCB LED Module made by Yuji International Co., Ltd., and a blue-light emitter comprising a 60 Watt series of blue-light emitting LED modules commercially available under the brand name LEDENET 20" Super Bright 30 LEDs 5050 Aquarium LED Strip-Waterproof Aluminum Lighting 12V DC. The light emitters were assembled into an enclosure having a prismatic diffuser, to provide a spatially homogeneous output. The white-light LED module was driven by a 24V dimmable power supply, enabling the adjustment of the relative luminous flux of the white-light emitter between zero and 100 percent of its power. The lighting assembly was positioned two feet above the surface of a table, and the surface of the table was illuminated with the lambertian output beam of the illuminant. The white-light emitter was adjusted to the zero percent (off) position, and the room lights turned off. Using a spectrophotometer, the spectral radiance was measured at a variety of locations within the output beam and confirmed to be reasonably uniform. The spectral radiant flux of the example is shown in the graph of FIG. 4, wherein the narrow-band emission feature at 589 nanometers 401 corresponds to the summed outputs of the two sodium lamps, and a second narrow-band emission feature 402 located at 455 nanometers corresponds to the summed outputs of the blue LEDs.

With ordinary room lighting active, the ambient level of lighting was measured to be 400 lux on the surface of the table using a hand-held luxmeter. This is a typical illumination level for an indoor office. With the room lighting turned off, the illumination assembly was activated and its white light component set to the off position. The amount of illumination was measured to be 2300 lux on the same table surface, with the detector located in the center of the output beam. To evaluate the subjective appearance of colors under the illumination assembly, a Munsell Color Checker was placed on the table in the center of the output beam. The table of FIG. 7 tabulates some of the properties of the Munsell Color Checker. The Munsell Color Checker consists of a grid of color swatches, organized into 4 rows of 6 swatches, indexed according to the "Index" column in FIG. 7. Each swatch has a corresponding Munsell-notation color that defines the spectral reflectance of that swatch. The swatches are also given canonical names such as "Dark skin", "Light skin" etc. as given in the "Munsell Description" column. The swatches also have CIE xy chromaticity coordinates which are given according to Munsell in the "Reference CIE xy" column.

With the Munsell Color Checker positioned as described above relative to the illumination assembly, and having the room lights off and the white-light emitter of the assembly in the off position, the Munsell Color Checker is essentially only illuminated with blue and yellow light. The effect of this illumination can be compared to dichromatic color vision. Under this lighting condition, the colors of the Munsell Color Checker swatches were noted, and are given in the table of FIG. 7 in the column "Description with Y+B Light". It may be appreciated here how color information related to the red-green axis of color space is invisible to the observer. For example at index 14 and 15, the colors normally described as "Green" and "Red" respectively are "Brown" and "Dark Brown", i.e. are indistinguishable hues. In addition, the dichromatic color rendering causes purple colors (e.g. index 8 and 10) to appear as shades of blue.

With the lighting conditions as described above, the Munsell Color Checker was then observed through an EnChroma Cx-65 lens. For an observer with normal color vision, there was no apparent change in the colors and the names provided under "Description with Y+B Light" remained the same. Next, the colors were observed through an EnChroma Cx-14 lens. For an observer with normal color vision, there was no apparent change in the colors and the names provided under "Description with Y+B Light" remained the same.

Next, the room lights were turned on so that the Munsell Color Checker was illuminated by a combination of ambient room lighting (fluorescent white lamps mounted on the ceiling), plus the blue and yellow narrow-band lighting of the illumination assembly. The lighting level on the surface of the table was again measured with a luxmeter and noted to be 2700 lux. This light is understood to be a combination of about 400 lux of ambient room lighting plus 2300 lux of narrow-band blue and yellow lighting. The combination of narrow-band and broad-band lighting produced a new subjective experience of the colors in the Munsell Color Checker, given in the column "Description with Y+B+W Light". These lighting conditions can be compared to the vision of a person with anomalous trichromacy, which is the most common type of red-green color blindness. These individuals have some sensitivity to red and green colors, but find the differences between red and green hues to be lesser in magnitude compared to an observer with normal color vision. Viewing the Munsell Color Checker under these conditions, an observer with normal color vision gave the descriptions given in "Description with Y+B+W Light". It may be noted in these descriptions that some amount of redness versus greenness in color is apparent. For example the color swatches nominally described as "Green" and "Red" were described as "Greenish Brown" and "Reddish Brown".

With the lighting conditions as described above, the Munsell Color Checker was then observed through an EnChroma Cx-65 lens. For an observer with normal color vision, there was a significant change in the colors. The color names as viewed by an observer with normal color vision through the glasses in these conditions are given in the column titled "Y+B+W with Glasses". It may be readily appreciated that the color names are essentially consistent with the "Munsell Description" names. Next, the colors were observed through an EnChroma Cx-25 lens. For an observer with normal color vision, a similar change of color perception was observed. The apparent colors seen were consistent with the names given under "Y+B+W with Glasses" but also had a greater color purity when compared to their appearance when viewed through the EnChroma Cx-65 glasses.

In a third set of lighting conditions, the ambient room lights were turned off, and then the white-light emitting LEDs in the illumination assembly were enabled and adjusted until a surface illumination of 2800 lux was recorded at the surface of the table in the center of the output beam. The observations of colors and trials with eyewear were repeated and gave identical results as in the prior condition using ambient room lighting. Therefore, the inclusion of a broad-band white-light emitter into the illumination assembly can be used to supplement ambient lighting conditions when the method and apparatus are employed in dark rooms. The white-light emitter may be manually adjusted by an observer to achieve the desired result, or may be automatically adjusted, for example by use of an ambient light sensor, the integrated white-light emitter may be automatically adjusted to achieve a consistent level of surface illumination between 2800 lux to 3200 lux.

The above teachings facilitate a method for demonstrating eyewear comprising a narrow-band spectral absorptive feature. Whereas the spectral features of such eyewear are not readily observable with the naked eye, and the function features of such eyewear may be difficult to appreciate in certain lighting conditions typical of indoor offices, the illumination assembly may be used to enhance the appreciation of the functional properties of narrow-band absorbing glasses in an indoor office, such as a retail store.

In a second example, the illuminant as constructed above may be configured within an enclosure with windows having a plurality of spectral transmittance characteristics. For example one (reference) window may have a neutral density 25% spectral transmittance (also called an ND25 filter), and a second (trial) window may be provided with the transmittance equivalent to the EnChroma Cx-25 lens. To enable automatic operation, the illumination assembly may be equipped with an ambient light sensor that automatically modulates the intensity of the white-light emitter to achieve a surface illumination of not less than 2800 lux inside the enclosure. In this arrangement, an observer looking through the first window would see the Munsell Color Checker as having the names tabulated under "Description with Y+B+W Light" in FIG. 7, but when looking through the second window would see the Munsell Color Checker as having the names tabulated under "Y+B+W with Glasses". The use of a neutral density filter (ND25) provides a consistent level of brightness of the illuminated scene through each window, however this normalization brightness is not essential to the method.

Various embodiments are described in the following clauses.

Clause 1. A lighting apparatus for simulating color vision deficiency, the apparatus comprising:

a yellow light emitter emitting yellow light comprising a narrow-band spectral peak with a maximum wavelength between 570 nanometers and 600 nanometers and a bandwidth of between 1 nanometers and 40 nanometers at half maximum;

wherein the yellow light is combined with white light having a color rendering index of at least 70 and a correlated color temperature between 2400K to 10000K to form an output beam;

wherein the luminous flux of white light in the output beam is at least one tenth the luminous flux of yellow light in the output beam; and wherein the luminous flux is measured with a lux meter anywhere within the central ten degrees of the output beam of the lighting apparatus.

Clause 2. The lighting apparatus of clause 1, wherein at least a portion of the white light is emitted by a white light emitter incorporated into the lighting apparatus.

Clause 3. The lighting apparatus of clause 2, comprising a power intensity modulator configured to control and vary the amount of white light emitted by the white light emitter.

Clause 4. The lighting apparatus of clause 3, comprising a light sensor that in combination with the power intensity modulator measures and controls the amount of white light in the output beam to ensure that there is at least a minimum amount of white light in the output beam.

Clause 5. The light apparatus of clause 4, wherein the minimum amount of white light in the output beam is satisfied by a combination of white light emitted by the white light emitter and ambient white light.

Clause 6. The lighting apparatus of any of clauses 3-5, wherein the minimum amount of white light in the output beam may be controlled and varied within the range of at least 10% of the luminous intensity of the yellow light to at least 150% of the luminous intensity of the yellow light.

Clause 7. The lighting apparatus of any of clauses 1-6, comprising a blue light emitter; wherein the blue light emitter emits blue light having a wavelength of maximum emission between 440 nanometers and 490 nanometers and a half maximum spectral bandwidth of between 1 nanometers and 60 nanometers centered around the wavelength of maximum emission; and wherein the blue light is combined with the white light and the yellow light to form the output beam.

Clause 8. A system for demonstrating an optical filter designed to ameliorate the effects of color vision deficiency comprising:

a lighting apparatus as described in any of the clauses 1-7;
a colorful object under illumination by the lighting apparatus;
an optical path providing a view of the illuminated colorful object through a trial filter; and
an optical path providing a view of the illuminated colorful object bypassing the trial filter;
wherein the trial filter comprises a narrow-band spectral transmission feature comprising a spectral notch having a transmission minimum located between 570 and 600 nanometers and having a half-minimum width of 40 nanometers or less.

Clause 9. The system of clause 8 wherein the optical path providing a view of the illuminated colorful object bypassing the trial filter provides a view of the illuminated colorful object through a reference filter that does not have a narrow-band spectral transmission feature comprising a spectral notch having a transmission minimum located between 570 to 600 nanometers and having a half-minimum width of 40 nanometers or less.

Clause 10. The system of clause 9 wherein the reference filter has a white point chromaticity within 0.05 units of the trial filter in the CIE xy coordinate system.

Clause 11. The system of clause 9 wherein the reference filter has a white point chromaticity within 0.05 units of the trial filter in the CIE xy coordinate system, and the reference filter has a luminous transmittance of average daylight between 75% and 135% of the luminous transmittance of average daylight of the trial filter, and average daylight is defined by CIE Illuminant D65.

Clause 12. The system of any of clauses 8-11 wherein the trial filter is incorporated into an ophthalmic lens mounted in spectacle glasses.

Clause 13. The system of any of clauses 8-11 wherein the trial filter is incorporated into an ophthalmic lens mounted in a lorgnette.

Clause 14. The system of any of clauses 8-11 wherein the trial filter is incorporated into a window.

Clause 15. A method for demonstrating an ophthalmic lens designed to ameliorate the effects of color vision deficiency comprising:

providing to a person a first view of a colorful object as illuminated by a lighting apparatus;
providing to a person a second view of a colorful object as illuminated by a lighting apparatus and filtered by a trial filter;
wherein the lighting apparatus comprises any of the lighting apparatus of clauses 1-7; and
wherein the trial filter comprises a narrow-band spectral notch having a wavelength of minimum transmittance between 570 nanometers and 600 nanometers, and the mean spectral transmittance of the trial filter over a spectral band 20 nanometers wide centered at the wavelength of minimum transmittance is less than one half of the luminous transmittance of the ophthalmic lens.

This disclosure is illustrative and not limiting. Further modifications will be apparent to one skilled in the art in light of this disclosure. For example, where methods and steps described above indicate certain events occurring in certain order, those of ordinary skill in the art will recognize that the ordering of certain steps may be modified and that such modifications are in accordance with the inventions disclosed herein. Additionally, certain of the steps may be performed concurrently in a parallel process when possible, as well as performed sequentially as described above. Acts referred to herein as operations in a method or process may also be understood as "steps" in the method or process. Therefore, to the extent there are variations of the inventions disclosed herein, which are within the spirit of this disclosure or equivalent to the inventions disclosed herein, it is the intent that this disclosure and the claims it supports will cover those variations as well. All publications and patent applications cited in this disclosure are incorporated herein by reference in their entirety as if each individual publication or patent application were specifically and individually put forth herein.

What is claimed is:

1. A system for demonstrating an optical filter designed to ameliorate the effects of color vision deficiency comprising:

a lighting apparatus comprising a yellow light emitter emitting yellow light with a narrow-band spectral peak having a maximum wavelength between 570 nanometers and 600 nanometers and a band-width of between 1 nanometers and 40 nanometers at half maximum; and an optical filter designed to ameliorate the effects of color vision deficiency having a transmission spectrum comprising a spectral notch having a transmission minimum located between 570 and 600 nanometers and having a half-minimum width of 40 nanometers or less, wherein the lighting apparatus is configured to illuminate a colorful object which can be viewed by a person through the optical filter.

2. The system of claim 1 comprising a reference filter having a transmission spectrum that does not have a spectral notch having a transmission minimum located between 570 to 600 nanometers and having a half-minimum width of 40 nanometers or less.

3. The system of claim 1 wherein the optical filter is incorporated into an ophthalmic lens mounted in spectacle glasses.

4. The system of claim 1 wherein the optical filter is incorporated into an ophthalmic lens mounted in a lorgnette.

5. The system of claim 1 wherein the optical filter is incorporated into a window.

6. The system of claim 1 wherein the light apparatus comprises a white light emitter emitting white light, wherein the yellow light combined with the white light has a color rendering index of at least 70 and a correlated color temperature between 2400K to 10000K.

7. The system of claim 1, wherein the light apparatus comprises a blue light emitter emitting blue light having a wavelength of maximum emission between 440 nanometers and 490 nanometers and a half maximum spectral bandwidth of between 1 nanometers and 60 nanometers centered around the wavelength of maximum emission.

8. The system of claim 6, comprising a power intensity modulator configured to vary the amount of white light emitted by the white light emitter.

9. The system of claim 8, comprising a light sensor, the light sensor in combination with the power intensity modulator measures and controls the amount of white light emitted so that the luminous intensity of the white light may vary from 10% of the luminous intensity of the yellow light to 150% of the luminous intensity of the yellow light.

10. A method for demonstrating an ophthalmic lens designed to ameliorate the effects of color vision deficiency comprising:
illuminating a colorful object with a lighting apparatus comprising a yellow light emitter emitting yellow light with a narrow-band spectral peak having a maximum wavelength between 570 nanometers and 600 nanometers and a band-width of between 1 nanometers and 40 nanometers at half maximum;
providing to a person a first view of the colorful object illuminated by the lighting apparatus; and
providing to the person a second view of the colorful object illuminated by the lighting apparatus and filtered by an optical filter, the optical filter having a transmission spectrum comprising a spectral notch having a transmission minimum located between 570 and 600 nanometers and having a half-minimum width of 40 nanometers or less.

11. The method of claim 10, wherein providing to a person the first view comprises providing the first view filtered by a reference filter, a reference filter having a transmission spectrum that does not have a spectral notch having a transmission minimum located between 570 to 600 nanometers and having a half-minimum width of 40 nanometers or less.

12. The method of claim 10, comprising providing glasses incorporating the optical filter to the person.

13. The method of claim 10, wherein the light apparatus comprises a white light emitter emitting white light, wherein the yellow light combined with the white light has a color rendering index of at least 70 and a correlated color temperature between 2400K to 10000K.

14. The method of claim 10, wherein the light apparatus comprises a blue light emitter emitting blue light having a wavelength of maximum emission between 440 nanometers and 490 nanometers and a half maximum spectral bandwidth of between 1 nanometers and 60 nanometers centered around the wavelength of maximum emission.

15. The method of claim 13, comprising varying the amount of white light emitted by the white light emitter.

16. The method of claim 15, comprising varying the luminous intensity of the white light within the range from 10% of the luminous intensity of the yellow light to 150% of the luminous intensity of the yellow light.

* * * * *